(12) United States Patent
Ogawa et al.

(10) Patent No.: US 10,472,344 B2
(45) Date of Patent: *Nov. 12, 2019

(54) FACTOR XIA INHIBITORS

(71) Applicant: MERCK SHARP & DOHME CORP., Rahway, NJ (US)

(72) Inventors: Anthony K. Ogawa, South San Francisco, CA (US); Linda Brockunier, Orange, NJ (US); James Tata, Westfield, NJ (US); Dann L. Parker, Jr., Cranford, NJ (US); Ming Wang, Belle Mead, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/780,134

(22) PCT Filed: Nov. 29, 2016

(86) PCT No.: PCT/US2016/063893
§ 371 (c)(1),
(2) Date: May 30, 2018

(87) PCT Pub. No.: WO2017/095760
PCT Pub. Date: Jun. 8, 2017

(65) Prior Publication Data
US 2018/0370947 A1    Dec. 27, 2018

Related U.S. Application Data

(60) Provisional application No. 62/262,099, filed on Dec. 2, 2015.

(51) Int. Cl.
*C07D 401/10* (2006.01)
*C07D 401/14* (2006.01)
*C07D 409/14* (2006.01)
*A61P 7/02* (2006.01)

(52) U.S. Cl.
CPC ........... *C07D 401/10* (2013.01); *A61P 7/02* (2018.01); *C07D 401/14* (2013.01); *C07D 409/14* (2013.01)

(58) Field of Classification Search
CPC ................. C07D 401/10; A61P 7/02
See application file for complete search history.

(56) References Cited

U.S. PATENT DOCUMENTS

| | | | | |
|---|---|---|---|---|
| 8,598,206 B2 | 12/2013 | Herold et al. | | |
| 9,783,530 B2* | 10/2017 | Liu | ............. | C07D 401/14 |
| 9,868,727 B2* | 1/2018 | Liu | ............. | C07D 401/14 |
| 10,011,585 B2* | 7/2018 | Liu | ............. | C07D 401/14 |
| 10,081,617 B2* | 9/2018 | Mertz | ............. | C07D 401/14 |
| 10,123,995 B2* | 11/2018 | Mertz | ............. | C07D 221/04 |
| 2004/0209921 A1 | 10/2004 | Bridger et al. | | |
| 2017/0197953 A1 | 7/2017 | Liu et al. | | |
| 2017/0210732 A1 | 7/2017 | Liu et al. | | |
| 2017/0240523 A1 | 8/2017 | Liu et al. | | |
| 2017/0240524 A1 | 8/2017 | Mertz et al. | | |
| 2018/0000795 A1 | 1/2018 | Mertz et al. | | |

FOREIGN PATENT DOCUMENTS

| | | |
|---|---|---|
| WO | 2005123680 A1 | 12/2005 |
| WO | 2007070826 A1 | 6/2007 |

OTHER PUBLICATIONS

Corte, et al., Pyridine and pyridinone-based factor XIa inhibitors, Bioorganic & Medicinal Chemistry Letters, 2015, 925-932, 25.
Haginoya, et al., Design, synthesis, and biological activity of non-amidine factor Xa inhibitors containing pyridine N-oxide and 2-carbamoylthiazole units, Bioorganic & Medicinal Chemistry, 2004, 5579-5586, 12(21).
Hu, et al, Discovery of a Potent Parenterally Administered Factor XIa Inhibitor with Hydroxyquinolin-2(1H-one ans the P2' Moiety, Medicinal Chemistry Letters, 2015, 590-595, 6.
International Search Report and Written Opinion for PCT/US2016/063893, dated Mar. 10, 2017, 8 pages.
Pinto, et al., Structure-based design of inhibitors of coagulation factor XIa withNoval P1 moieties, Bioorganic & Medicinal Chemistry Letters, 2015, 1635-1642, 25.
Supplementary European Search Report for 16871331.1, dated Apr. 10, 2019; 6 pages.

* cited by examiner

Primary Examiner — Golam M Shameem
(74) Attorney, Agent, or Firm — Nicole M. Beeler; John C. Todaro

(57) ABSTRACT

The present invention provides a compound of Formula I and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

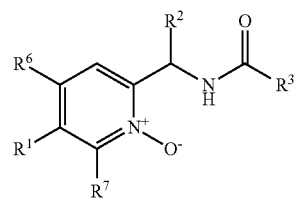

10 Claims, No Drawings

FACTOR XIA INHIBITORS

CROSS REFERENCE TO RELATED APPLICATIONS

This application is a U.S. National Phase application under 35 U.S.C. § 371 of PCT Application No. PCT/US2016/063893 filed Nov. 29, 2016, which claims priority from U.S. Ser. No. 62/262,099 filed Dec. 2, 2015.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel, blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

Plasma kallikrein is a zymogen of a trypsin-like serine protease and is present in plasma. The gene structure is similar to that of factor XI. Overall, the amino acid sequence of plasma kallikrein has 58% homology to factor XI. Proteolyticactivation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability andvasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on C1-esterase inhibitor suffer from hereditary angioedema (HAE), a life-long disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clinimmunol., 120: p. 416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

Factor XIa inhibitor compounds are described in WO2015047973, WO2015054087, WO2015123090, WO2015123091, WO2015123093, WO2015164308, WO2014160592, WO2013022814, WO 2013022814, WO 2013022818, WO 2013055984, WO2013056034, WO2013056060, WO2013118805. WO2013093484.WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

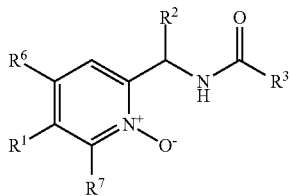

and pharmaceutically acceptable salts thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

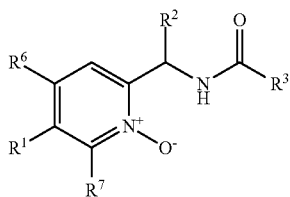

wherein $R^1$ is aryl or heteroaryl, wherein said aryl and heteroaryl groups are optionally substituted with one to three substituents independently selected from the group consisting of halo, nitro, cyano, oxo, $R^4$, $OR^4$, $C(O)R^4$, $C(O)OR^4$, $NR^4R^5$, $C_{1-3}$ alkyl-$NR^4R^5$, $NHC(O)R^4$, $NHC(O)OR^4$, $C_{3-6}$ cycloalkyl and heteroaryl (which is optionally substituted with halo, cyano, $C(O)NR^4R^5$ or $R^4$);

$R^2$ is hydrogen or $CH(R^{2a})(R^{2b})$;

$R^{2a}$ is $C_{1-6}$ alkyl, aryl, heteroaryl, $C_{3-6}$ cycloalkyl or heterocyclyl, wherein said alkyl group is optionally substituted with one to three substituents independently selected from the group consisting of halo, cyano and $OR^4$, and wherein said aryl, heteroaryl, cycloalkyl and heterocyclyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, $C(O)R^4$, $C(O)OR^4$, $C(O)NR^4R^5$, $NR^4R^5$, $NHC(O)R^4$, $NHC(O)OR^4$, $NHC(O)C_{1-4}$alkyl-$OR^4$ and heteroaryl;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is hydrogen, cyano, halo, $R^4$ or $OR^4$;

$R^7$ is hydrogen, cyano, halo, $R^4$ or $OR^4$;

or a pharmaceutically acceptable salt thereof.

An embodiment of the present invention relates to compounds of Formula Ia:

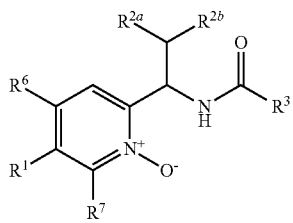

wherein $R^1$ is aryl or heteroaryl, wherein said aryl and heteroaryl groups are optionally substituted with one to three substituents independently selected from the group consisting of halo, nitro, cyano, oxo, $R^4$, $OR^4$, $C(O)R^4$, $C(O)OR^4$, $NR^4R^5$, $C_{1-3}$ alkyl-$NR^4R^5$, $NHC(O)R^4$, $NHC(O)OR^4$, $C_{3-6}$ cycloalkyl and heteroaryl (which is optionally substituted with $R^4$);

$R^{2a}$ is $C_{1-6}$ alkyl, aryl, heteroaryl, $C_{3-6}$ cycloalkyl or heterocyclyl, wherein said alkyl group is optionally substituted with one to three substituents independently selected from the group consisting of halo, cyano and $OR^4$, and wherein said aryl, heteroaryl, cycloalkyl and heterocyclyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, $C(O)R^4$, $C(O)OR^4$, $C(O)NR^4R^5$, $NR^4R^5$, $NHC(O)R^4$, $NHC(O)OR^4$, $NHC(O)C_{1-4}$alkyl-$OR^4$ and heteroaryl;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is hydrogen, cyano, halo, $R^4$ or $OR^4$;

$R^7$ is hydrogen, cyano, halo, $R^4$ or $OR^4$;

or a pharmaceutically acceptable salt thereof.

An embodiment of the present invention relates to compounds of Formula Ib:

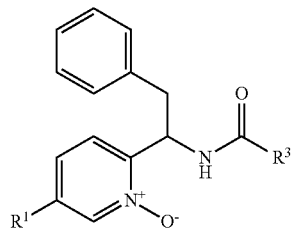

Ib wherein $R^1$ is aryl or heteroaryl, wherein said aryl and heteroaryl groups are optionally substituted with one to three substituents independently selected from the group consisting of halo, nitro, cyano, oxo, $R^4$, $OR^4$, $C(O)R^4$, $C(O)OR^4$, $NR^4R^5$, $C_{1-3}$ alkyl-$NR^4R^5$, $NHC(O)R^4$, $NHC(O)OR^4$, $C_{3-6}$ cycloalkyl and heteroaryl (which is optionally substituted with $R^4$);

$R^3$ is aryl, heteroaryl, $C_{3-10}$ cycloalkyl or heterocycyl, wherein said aryl, heteroaryl, cycloalkyl and heterocyclyl groups are optionally substituted with one to three substituents independently selected from the group consisting of halo, nitro, cyano, oxo, $R^4$, $OR^4$, $C(O)R^4$, $C(O)OR^4$, $C(O)NR^4R^5$, $NR^4R^5$, $NHC(O)R^4$, $NHC(O)OR^4$, $NHC(O)C_{1-4}$alkyl-$OR^4$ and heteroaryl;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

or a pharmaceutically acceptable salt thereof.

In an embodiment of the invention, $R^1$ is phenyl, which optionally is substituted with one to three substituents independently selected from the group consisting of chloro, fluoro, $C_{3-6}$ cycloalkyl and heteroaryl (which is optionally substituted with $R^4$). In a class of the embodiment, $R^1$ is phenyl, which optionally is substituted with two or three substituents independently selected from the group consisting of chloro and tetrazolyl.

In an embodiment of the invention, $R^{2a}$ is phenyl, which optionally is substituted with one to three halo.

In an embodiment of the invention, $R^{2b}$ is hydrogen.

In an embodiment of the invention, $R^3$ is aryl or heteroaryl, wherein said aryl and heteroaryl groups are optionally substituted with one to three substituents independently selected from the group consisting of $C(O)OR^4$, $C(O)NR^4R^5$, $NR^4R^5$, $NHC(O)OR^4$, $NHC(O)C_{1-4}$alkyl-$OR^4$. In a class of the embodiment, $R^3$ is phenyl, thiophenyl or indazolyl, wherein said phenyl, thiophenyl and indazolyl groups are optionally substituted with $C(O)OR^4$, $C(O)NR^4R^5$, $NR^4R^5$, $NHC(O)OR^4$, $NHC(O)C_{1-4}$alkyl-$OR^4$.

In an embodiment of the invention, $R^6$ is hydrogen.

In an embodiment of the invention, $R^7$ is hydrogen.

Reference to the preferred classes and subclasses set forth above is meant to include all combinations of particular and preferred groups unless stated otherwise.

Specific embodiments of the present invention include, but are not limited to the compounds identified herein as Examples 1 to 7, or pharmaceutically acceptable salts thereof.

Also included within the scope of the present invention is a pharmaceutical composition which is comprised of a compound of Formula I, Formula Ia or Formula Ib as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

It will be understood that, as used herein, references to the compounds of structural Formula I, Formula Ia and Formula Ib are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemi sulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I, Formula Ia or Formula Ib simultaneously contain acidic and basic groups in the molecule the invention also includes, in addition to the salt forms mentioned, inner salts or betaines (zwitterions).

The present invention encompasses all stereoisomeric forms of the compounds of Formula I, Formula Ia and Formula Ib. Unless a specific stereochemistry is indicated, the present invention is meant to comprehend all such isomeric forms of these compounds. Centers of asymmetry that are present in the compounds of Formula I, Formula Ia and Formula Ib can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enationmer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the transform as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula Ia or Formula Ib or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($1_H$) and deuterium ($2_H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I, Formula Ia and Formula Ib are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the terms "alkyl" and "alkylene" are intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

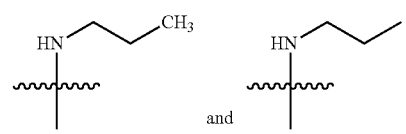

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S.

Bicyclic heteroaryl ring systems include fused ring systems, where two rings share two atoms, and spiro ring systems, where two rings share one atom. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetrahydroquinoline and 3-oxo-3,4dihydro-2N-benzo[b][1,4]thiazine. If the heteroaryl contains nitrogen atoms, it is understood that the corresponding N-oxides thereof are also encompassed by this definition.

Except where noted, the term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

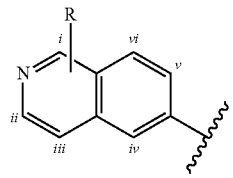

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also relates to medicaments containing at least one compound of the Formula I, Formula Ia or Formula Ib and/or of a pharmaceutically acceptable salt of the compound of the Formula I, Formula Ia or Formula Ib and/or an optionally stereoisomeric form of the compound of the Formula I, Formula Ia or Formula Ib or a pharmaceutically acceptable salt of the stereoisomeric form of the compound of Formula I, Formula Ia or Formula Ib, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specificed otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I, Formula Ia and Formula Ib can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACANDC®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVANC®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin, remogliflozin and sotagliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

For purposes of this specification, the following abbreviations have the indicated meanings:
Ac acetyl
ACN acetonitrile
AcOH or HOAc acetic acid
aq aqueous
Bn benzyl
Boc or BOC tert-butoxycarbonyl
BOP reagent benzotriazol-1-yloxy tris(dimethylamino)phosphonium hexafluorophosphate
BOP-Cl bis(2-oxo-3-oxazolidinyl)phosphinic chloride
Bu butyl
Bz benzoyl
cBu cyclobutyl
Cbz benyzloxycarbonyl
cPr cyclopropyl
DCC 1,4-dicyclohexylcabodiimide
DCE 1,2-dichloroethane
DCM dichloromethane
DIEA or Hunig's base N,N-diisopropylethylamine
DMF dimethylformamide
DMSO dimethyl sulfoxide
dppf 1,1'-bis(diphenylphosphino)ferrocene
Et ethyl
EtOAc ethyl acetate
g grams
h hour
HATU N,N,N',N'-tetramethyl-O-(7-azabenzotriazol-1-yl)uronium hexafluorophosphate
HPLC high-performance liquid chromatography
IPA isopropanol
iPr isopropyl
LCMS liquid chromatography mass spectrometry
LDA lithium diisopropylamide
Me methyl
MeOH methanol
mg milligrams
min minute
μL microliters
mL milliliters
mmol millimoles
MS mass spectrometry
Ms methanesulfonyl (mesyl)
MTBE methyl tert-butyl ether
NMR nuclear magnetic resonance spectroscopy
Ph phenyl
Pr propyl
rac racemic mixture
RT or rt room temperature (ambient, about 25° C.)
SFC supercritical fluid chromatography
tBu tert-butyl
TEA triethylamine ($Et_3N$)
TFA trifluoroacetic acid
THF THF
TLC thin layer chromatography
TMS trimethylsilyl
Ts toluenesulfonyl (tolyl)
WSC-HCl 1-ethyl-3-(3'-dimethylaminopropyl)carbodiimide hydrochloride Also, TLC is thin layer chromatography; UV is ultraviolet; W is watts; wt. % is percentage by weight; x g is times gravity; $\alpha_D$ is the specific rotation of polarized light at 589 nm; ° C. is degrees Celsius; % w/v is percentage in weight of the former agent relative to the volume of the latter agent; Hz is hertz; cpm is counts per minute; $\delta_H$ is chemical shift; d is doublet; dd is doublet of doublets; MHz is megahertz; MS is mass spectrum, and a mass spectrum obtained by ES-MS may be denoted herein by "LC-MS"; m/z is mass to charge ratio; n is normal; N is normal; nm is nanometer; nM is nanomolar.

"Human FXIa Ki (nm)" is Human Factor XIa Ki (nm).

LCMS conditions: column: SUPELCO Ascentis Express C18 3×100 mm, 2.7 um. Solvent system: A—0.05% TFA in water and B—0.05% TFA in Acetonitrile. Gradient condition: 10% B to 99% B in 3.5 min.

General Methods

Compounds of the present invention may be prepared using conventional techniques or according to the methodology outlined in the following general synthetic schemes.

SCHEME A

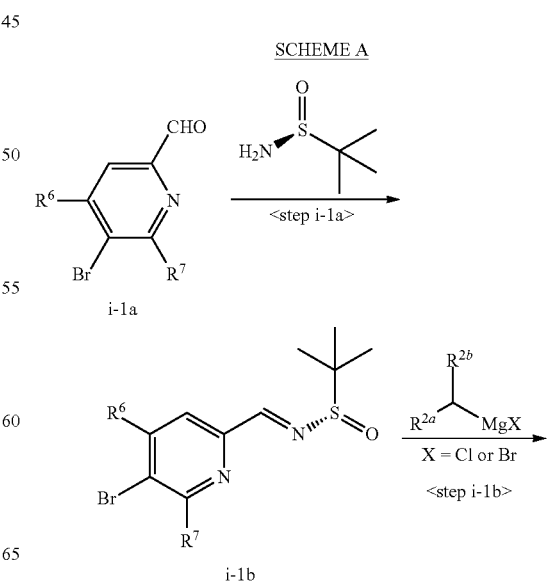

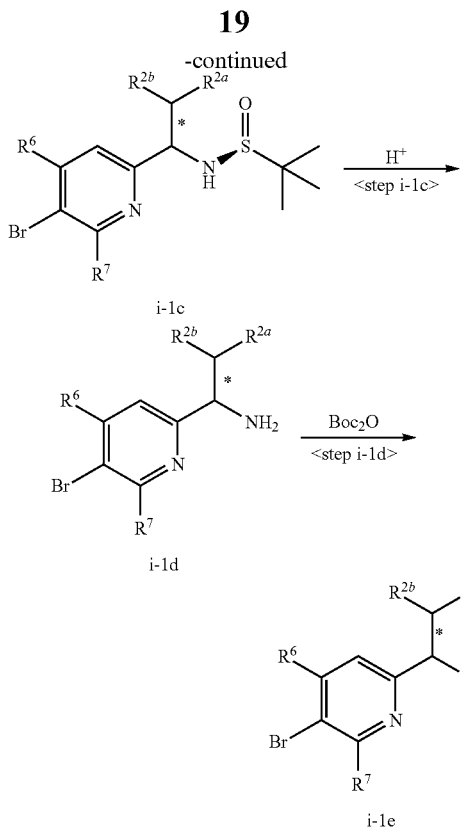

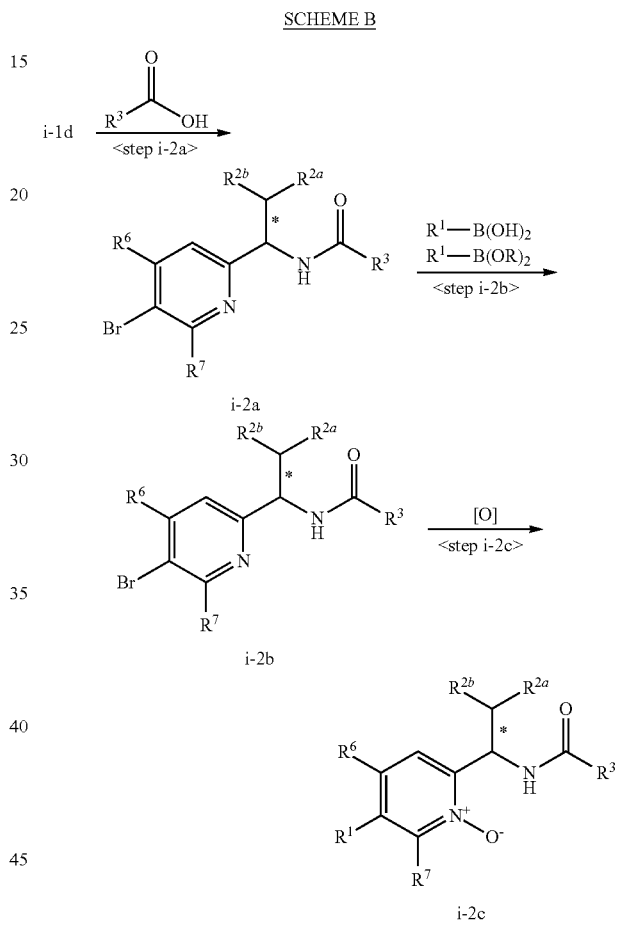

<Step i-1a> A compound represented by formula i-1b can be prepared by treating an aldehyde represented by i-1a with a suitable sulfinamide. Sulfinamide reagents are commonly purchased from commercial sources in enantiomerically pure form. The reaction is promoted by the use of a suitable dehydrating agent, such as $CuSO_4$, $MgSO_4$, $Ti(OiPr)_4$, or the like, and is typically performed in an inert solvent, such as DCM or THF, at room temperature (reviewed in: Ellman, J. A. et al. *Acc. Chem. Res.* 2002, 35, 984-995).

<Step i-1b> Step i-1b describes a method of synthesis of sulfinamides (i-1b) by the addition of an organometallic reagent (($R^{2a}$)($R^{2b}$)CHMgX) capable of transferring an aryl or alkyl group, to a sulfinyl imine (i-1a). Preferred organometallic reagents for effecting this transformation include organomagnesium (Grignard), organolithium and organozinc compounds. It is customary to conduct the reaction in a suitable inert solvent such as THF, diethyl ether, toluene, or the like, at reduced temperatures between −78° C. and the boiling temperature of the solvent. The Grignard, organolithium or organozinc reagents are commonly purchased from commercial sources, but can be prepared synthetically according to known methods of organic synthesis. The product of this reaction (i-1c) is commonly enriched in the stereochemistry transferred by the chiral auxiliary, which can be inferred based on literature precedent (reviewed in: Ellman, J. A. et al. *Acc. Chem. Res.* 2002, 35, 984-995).

<Step i-1c> A compound represented by formula i-1d can be prepared by treating a sulfinamide (i-1c) with a suitable acid, such as hydrogen chloride in a suitable solvent, such as EtOAc, or MeOH. The deprotection is commonly conducted typically at temperatures between 0° C. and room temperature, and the reaction is usually complete in 0.5-3 hours. The product amine (i-1d) can be used as a coupling partner or elaborated using a variety of methods known in organic synthesis.

<Step i-1d> A compound represented by formula i-1e can be prepared by treating an amine (i-1d) with Boc-reagent, such as $Boc_2O$ or Boc-ON, in the presence of a suitable base, such as triethylamine, DIEA, or the like using a variety of methods known in organic synthesis. Alternatively, Boc-protection may be performed in the presence of a weak inorganic base, such as sodium bicarbonate or sodium carbonate. Reactions are typically performed in a biphasic solvent system, such as 1,4-dioxane and water, under a variety of conditions known in organic synthesis.

<Step i-2a> A compound represented by formula (i-2a) can be produced by allowing an amine (i-1d) to react with a carboxylic acid ($R^3$—$CO_2H$) by a well-known or a process similar to that described in published documents (for example, Organic synthesis IV, Acids, amino acids, and peptides, pp. 191-309, 1992, Maruzen Co., Ltd.), in the presence of a condensing agent such as 1,3-dicyclohexyl-carbodiimide (DCC), 1-ethyl-3-(3'-dimethylaminopropyl) carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)phosphonium hexafluorophosphate (BOP reagent), or bis(2-oxo-3-oxazolidinyl)phosphinic chloride (BOP-Cl), in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature.

<Step i-2b> A compound represented by formula (i-2b) can be produced by a method commonly referred to as the Suzuki coupling reaction. Compounds of type (i-2a) can be treated with an aryl- or heteroaryl-boronic acid of type $R^1$—$B(OH)_2$, or alternatively, an aryl- or heteroarylboronate of type $R^1$—$B(OR)_2$, in the presence of a suitable palladium catalyst, such as [1,1'-bis(diphenylphosphino)ferrocene]-dichloropalladium(II), or tetrakis(triphenylphosphine)palladium (0), or the like, and a mild base, such as sodium carbonate, sodium phosphate tribasic, or the like (*Pure Appl. Chem.* 1991, 63, 419-422). The reaction is usually performed in a suitable degassed aqueous mixture of inert organic solvents, such as toluene, ethanol or dioxane, at elevated temperatures, generally between 70° C. and the boiling temperature of the solvent mixture, for a period of 3-24 h. Alternatively, those skilled in the art can perform the Suzuki reaction described above in a suitable vessel that enables heating in a microwave reactor to superheated reaction temperatures that can reduce reaction times to between 1 min and 1 h. Recently, conditions suitable for performing Suzuki reactions at room temperature have been published (for example, see: *J. Am. Chem. Soc.* 2000, 122, 4020-4028, and references therein).

<Step i-2c> A compound represented by formula (i-2c) can be produced by allowing the suitably substituted pyridine amide (i-2b) to react with an oxidizing reagent commonly refered to as a peroxide, such as hydrogen peroxide, meta-chloroperbenzoic acid, oxone, dimethyldioxirane, and peracitic acid in a proper solvent including water, methylene chloride and acetic acid. The reaction is usually performed at a temperature between 0 to 70° C. in a time period ranging from a few minutes to a few days. Such a process or processes are similar to that are described in published documents (For example, see, Deng, Lisheng; Sundriyal, Sandeep; Rubio, Valentina; Shi, Zheng-zheng; Song, Yongcheng, Journal of Medicinal Chemistry (2009), 52(21), 6539-6542).

SCHEME C

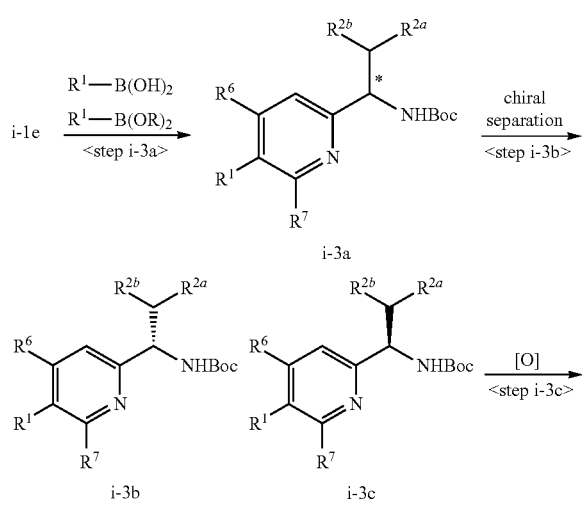

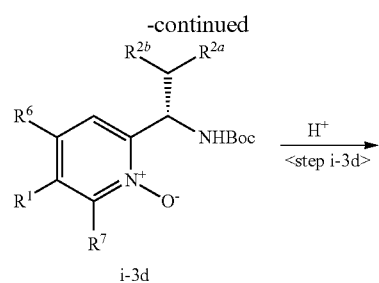

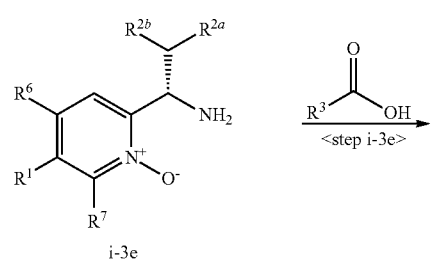

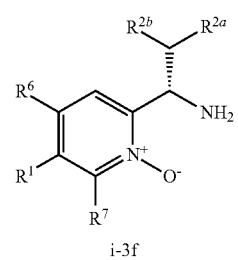

<Step i-3a> A compound represented by formula (i-3a) can be produced by reacting an aryl halide (i-1e) with a suitably substituted boronic acid ($R^1$—$B(OH)_2$) or boronate ester ($R^1$—$B(OR)_2$), as described above in Step i-2b.

<Step i-3b> Chiral resolution of compounds i-3b and i-3c can be performed wherein the asterisked carbon is a center of chirality. Generally, compound mixtures represented by the formula i-3a, or intermediates en route to their preparation, may be resolved to afford enantiomerically pure compounds by chiral stationary phase liquid chromatography techniques or other suitable methods known in organic synthesis.

<Step i-3c> A compound represented by formula (i-3d) can be produced by reacting a suitably substituted pyridine amide (i-3b), as described above in Step i-2c.

<Step i-3d> A compound represented by formula (i-3e) can be produced by reacting an N-Boc carbamate (i-3d) with hydrogen chloride in EtOAc or TFA in DCM. The deprotection is conducted typically at temperatures between 0° C. and room temperature, and the reaction is usually complete in 0.5-3 hours. The product amine (i-3e) can be used as a coupling partner or elaborated using a variety of methods known in organic synthesis.

<Step i-3e> A compound represented by formula (i-3f) can be produced by reacting an amine (i-3e) with a carboxylic acid ($R^3$—$CO_2H$), as described above in Step i-2a.

Example 1

(S)-2-(1-(3-AMMONIO-1H-INDAZOLE-6-CARBOXAMIDO)-2-PHENYLETHYL)-5-(5-CHLORO-2-(1H-TETRAZOL-1-YL)PHENYL)PYRIDINE 1-OXIDE 2,2,2-TRIFLUOROACETATE

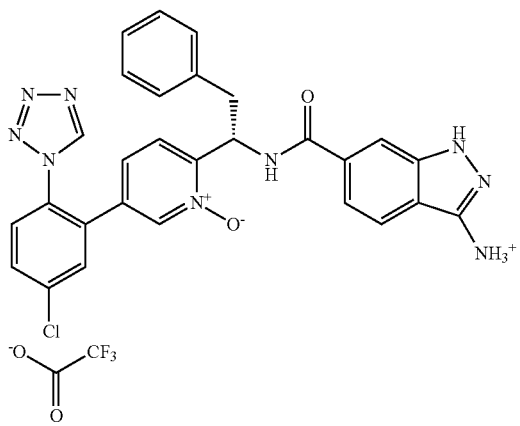

Step 1: Preparation of (E)-N-((5-bromopyridin-2-yl)methylene)-2-methylpropane-2-sulfinamide(1a)

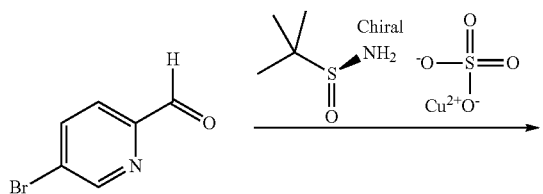

To a solution of (S)-(−)-2-methyl-2-propanesulfinamide (10.8 g, 89.0 mmol) and copper(II) sulfate (18.9 g, 118 mmol) in $CH_2Cl_2$ (200 ml) at 0° C. was added 5-bromopicolinaldehyde (10.0 g, 53.8 mmol) in several portions. The ice bath removed after 5 min, and the slurry was stirred at ambient temperature overnight. The reaction mixture was diluted with $CH_2Cl_2$ and filtered through a plug of celite, washing the filter pad well with $CH_2Cl_2$. The filtrate was concentrated in vacuo and purified by silica gel column chromatography using a gradient of 0-50% EtOAc/Hexanes as eluent to give the title compound (1a). LC-MS [M+H]: m/z 289.0. $^1$H NMR ($CHCl_3$-d, 500 MHz): $\delta_H$ 8.82-8.81 (1H, m), 8.68 (1H, s), 7.99-7.93 (2H, m), 1.30 (9H, s).

Step 2: Preparation of N-(1-(5-bromopyridin-2-yl)-2-phenylethyl)-2-methylpropane-2-sulfinamide (1b)

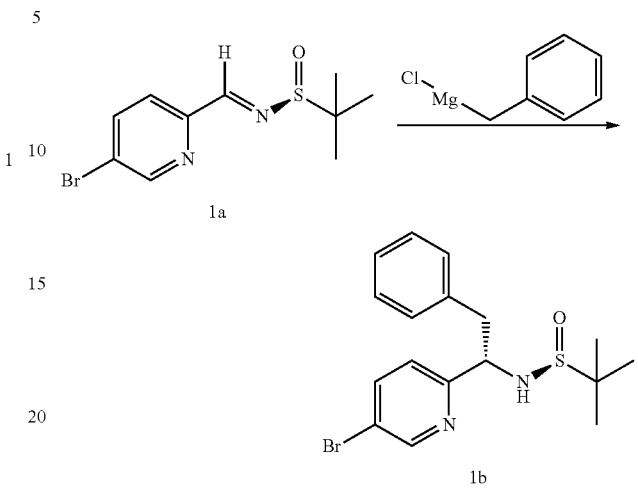

To a solution of 1a (5.00 g, 17.3 mmol) in $CH_2Cl_2$ (85 mL) at −50° C. under $N_2$ was added 2M benzylmagnesium chloride in THF (10.4 mL, 20.8 mmol) dropwise. The resultant solution was allowed to warm slowly to 5° C. over a period of 3 h, then the cold bath was removed and after 15 min the reaction was quenched by the addition of 2M $K_3PO_4$ and $H_2O$. The mixture was extracted with $CH_2Cl_2$ and the combined organic extracts were washed with $H_2O$ and brine. After drying over $MgSO_4$, the solution was filtered and concentrated in vacuo to provide the title compound (1b) as the major diasteromer, which was carried on without further purification. LC-MS [M+H]: m/z 381.2.

Step 3: Preparation of 1-(5-bromopyridin-2-yl)-2-phenylethan-1-amine (1c)

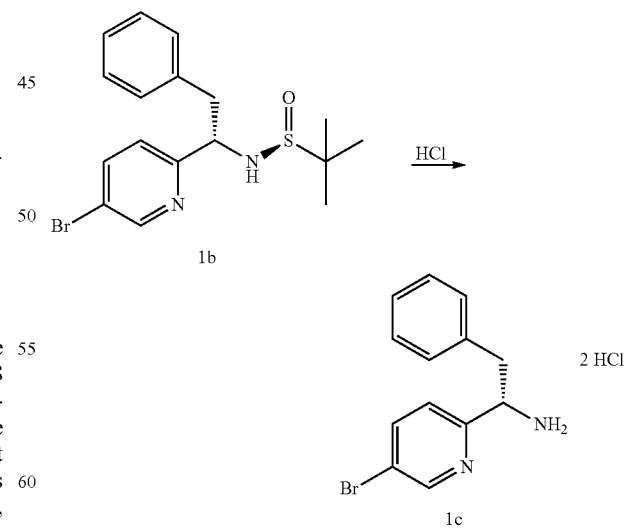

To a solution of 1b (6.60 g, 17.3 mmol) in MeOH (80 ml) at 0° C. was slowly added 4M HCl in dioxane (21.6 ml, 87 mmol). When the addition was complete, the cold bath was removed, and stirring continued at ambient temperature for 30 min. The mixture was concentrated in vacuo, azeotroping with MeOH several times. The solid residue was triturated with Et₂O to give the title compound (1c) as the major isomer, which was carried on without further purification. LC-MS [M+H]: m/z 277.1.

Step 4: Preparation of tert-butyl (1-(5-bromopyridin-2-yl)-2-phenylethyl)carbamate (1d)

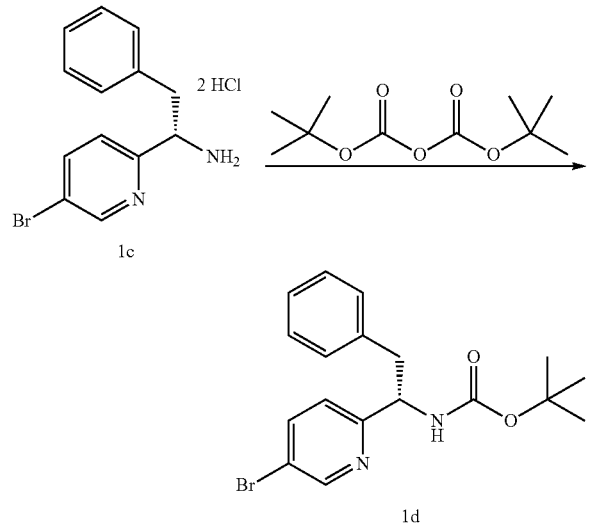

To a solution of 1c (6.06 g, 17.3 mmol) in CH₂Cl₂ (85 ml) at 0° C. was added BOC-Anhydride (4.4 ml, 19.0 mmol), followed by dropwise addition of DIEA (15 ml, 87 mmol). After 5 min, the cold bath was removed and the reaction mixture allowed to warm to ambient temperature over 45 min. The solution was washed with satd. aq. NaHCO₃ solution and brine, dried over MgSO₄, filtered, and concentrated in vacuo onto Celite®. It was purified by silica gel column chromatography using a gradient of 0-50% EtOAc/Hexanes as eluent to provide the title compound (1d) as the major isomer. LC-MS [M+H]: m/z=377.2. ¹H NMR (CHCl₃-d, 500 MHz): $\delta_H$ 8.64 (1H, s), 7.63 (1H, d, J=8.2 Hz), 7.22 (3H, d, J=9.1 Hz), 6.99 (2H, d, J=7.0 Hz), 6.77 (1H, d, J=8.3 Hz), 5.62 (1H, d, J=8.1 Hz), 4.95 (1H, d, J=8.1 Hz), 3.23-3.20 (1H, m), 3.03 (1H, dd, J=13.3, 8.0 Hz), 1.44 (9H, d, J=1.7 Hz).

Step 5: Preparation of tert-butyl (1-(5-(2-amino-5-chlorophenyl)pyridin-2-yl)-2-phenylethyl)carbamate (1e)

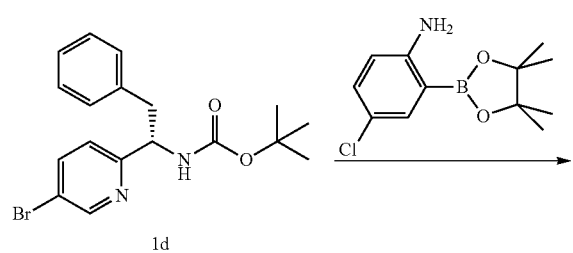

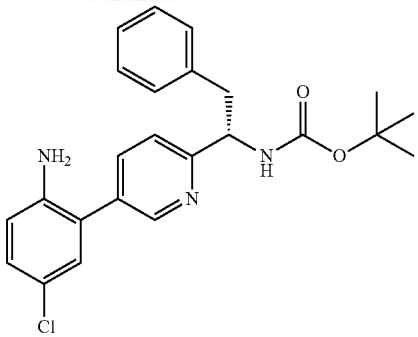

Compound 1d (793 mg, 2.10 mmol), 2-amino-5-chlorophenylboronic acid, pinacol ester (586 mg, 2.31 mmol), PdCl₂(dppf) (308 mg, 0.420 mmol), and cesium fluoride (958 mg, 6.31 mmol) were suspended in 1,4-dioxane (26 ml) in a sealed tube equipped with a septum. A stream of N₂ was bubbled through the solution for 10 min, then the mixture was heated in an oil bath at 110° C. for 30 min. The mixture was cooled, diluted with EtOAc, washed with H₂O and brine, dried over MgSO₄, filtered, and concentrated in vacuo. The residue was purified by silica gel column chromatography using a gradient of 0-100% EtOAc/Hexanes as eluent to give the title compond as (1e) as the major isomer. LC-MS [M+H]: m/z 424.3. ¹H NMR (CHCl₃-d, 500 MHz): $\delta_H$ 8.64 (1H, s), 7.61 (1H, d, J=8.0 Hz), 7.22-7.17 (3H, m), 7.17 (1H, m), 7.10-7.03 (3H, m), 6.99 (1H, d, J=8.0 Hz), 6.73 (1H, dd, J=8.5, 4.8 Hz), 5.73 (1H, d, J=8.1 Hz), 5.06 (1H, d, J=8.2 Hz), 3.69 (2H, s), 3.3-3.2 (1H, m), 3.11 (1H, dd, J=13.1, 7.7 Hz), 1.45 (9H, m).

Step 6: Preparation of tert-butyl (1-(5-(5-chloro-2-(1H-tetrazol-1-yl)phenyl)pyridin-2-yl)-2-phenylethyl)carbamate (1f)

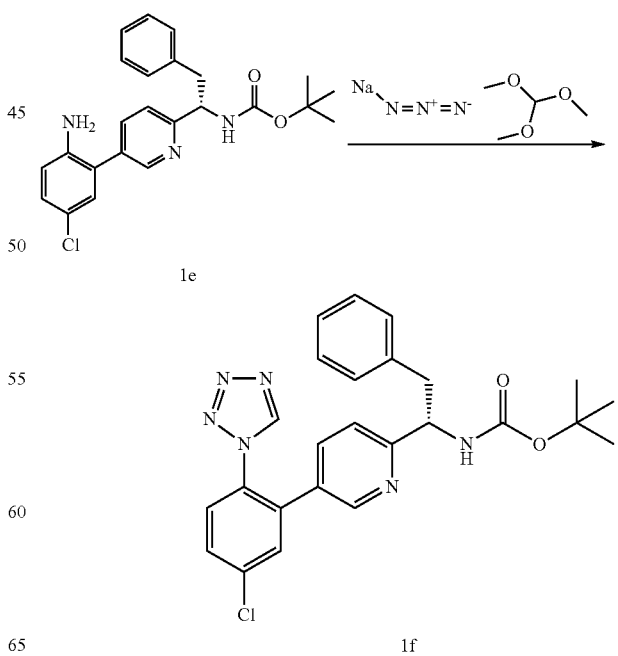

Compound 1e (844 mg, 1.99 mmol), sodium azide (647 mg, 9.95 mmol), and trimethyl orthoformate (1.10 ml, 9.95 mmol) were suspended in acetic acid (15 mL) and the resultant mixture was stirred at ambient temperature overnight. The mixture was partitioned between EtOAc and water, the layers separated, and the organic phase was washed with brine, dried over MgSO$_4$, filtered, and concentrated in vacuo, azeotroping with toluene several times. The residue was purified by silica gel column chromatography using a gradient of 0-70% EtOAc/Hexanes as eluent to provide the title compound (1f) as the major isomer. LC-MS [M+H]: m/z 477.3. $^1$H NMR (CHCl$_3$-d, 500 MHz): $\delta_H$ 8.34 (1H, s), 8.29 (1H, s), 7.64 (1H, dd, J=8.5, 2.3 Hz), 7.57 (2H, d, J=8.5 Hz), 7.26-7.19 (3H, m) 7.16 (1H, d, J=8.0 Hz), 6.92 (2H, d, J=7.4 Hz), 6.80 (1H, d, J=8.1 Hz), 5.66 (1H, s), 4.99 (1H, s), 3.22 (1H, br s), 3.01 (1H, dd, J=13.2, 8.1 Hz), 1.45 (9H, m).

Step 7: Preparation of tert-butyl (S)-(1-(5-(5-chloro-2-(1H-tetrazol-1-yl)phenyl)pyridin-2-yl)-2-phenylethyl)carbamate (1g)

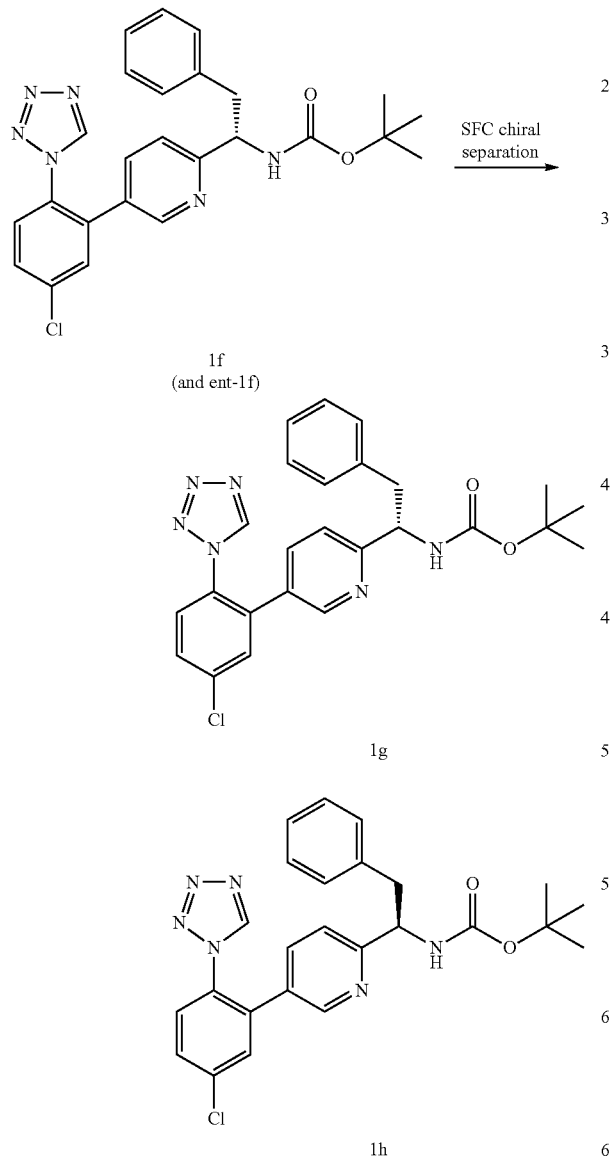

Compound 1f (and its enantiomer, ent-1f) (2.33 g, 4.89 mmol) was purified by chiral SFC chromatography using an OD-H column (2×25 cm) with 30% (1:1) MeOH:MeCN/CO$_2$, 100 bar, with 60 mL/min flow rate to give pure enantiomers (1g and 1h). Compound 1g: LC-MS [M+H]: m/z 477.0.

Step 8: Preparation of (S)-2-(1-((tert-butoxycarbonyl)amino)-2-phenylethyl)-5-(5-chloro-2-(1H-tetrazol-1-yl)phenyl)pyridine 1-oxide (1i)

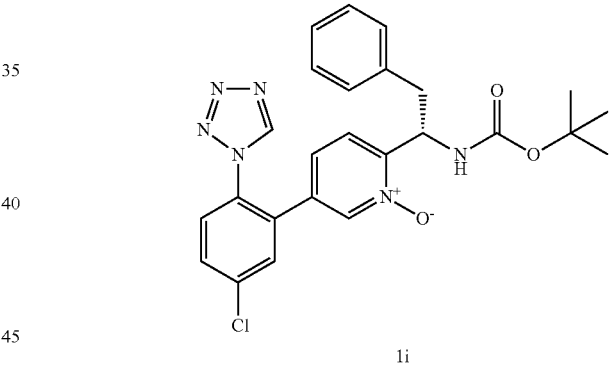

To a solution of 1g (50 mg, 0.105 mmol) in MeOH (1.5 mL) was added methyltrioxorhenium (VII) (13.1 mg, 0.052 mmol) followed by dropwise addition 35% aq. hydrogen peroxide (64.0 µl, 0.734 mmol). After stirring for 30 min, additional portions of methyltrioxorhenium (VII) (13.1 mg, 0.052 mmol) and 35% aq. hydrogen peroxide (64.0 µL, 0.734 mmol) were added. The mixture was stored at −5° C. for two days then stirring was continued for 7.5 hours at ambient temperature. The reaction was quenched with 10% aq. NaHSO$_3$, diluted with EtOAc, and the layers were separated. The organic phase was washed with 10% aq. NaHSO$_3$ and brine, dried over MgSO$_4$, filtered, and concentrated in vacuo to provide the title compound (1i) which was used in the next step without further purification. LC-MS [M+H]: m/z 493.2.

Step 9: Preparation of (S)-2-(1-amino-2-phenylethyl)-5-(5-chloro-2-(1H-tetrazol-1-yl)phenyl)pyridine 1-oxide (1j)

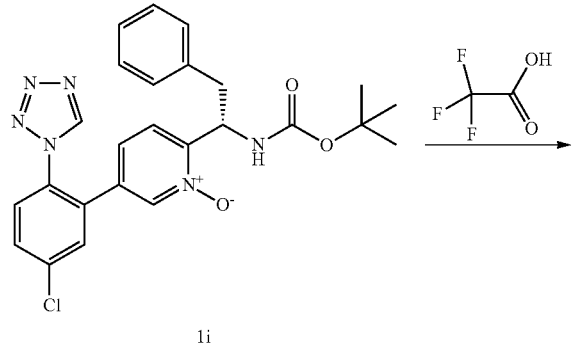

To a solution of 1i (52.0 mg, 0.105 mmol) in CH$_2$Cl$_2$ (3 mL) was added TFA (1.0 mL, 13.0 mmol) and stirring continued at rt for 15 min. The mixture was concentrated in vacuo, azeotroping several times from CH$_2$Cl$_2$ to give the title compound (1j) which was used in the next step without further purification. LC-MS [M+H]: m/z 393.2.

Step 10: Preparation of (S)-2-(1-(3-ammonio-1H-indazole-6-carboxamido)-2-phenylethyl)-5-(5-chloro-2-(1H-tetrazol-1-yl)phenyl)pyridine 1-oxide 2,2,2-trifluoroacetate (1)

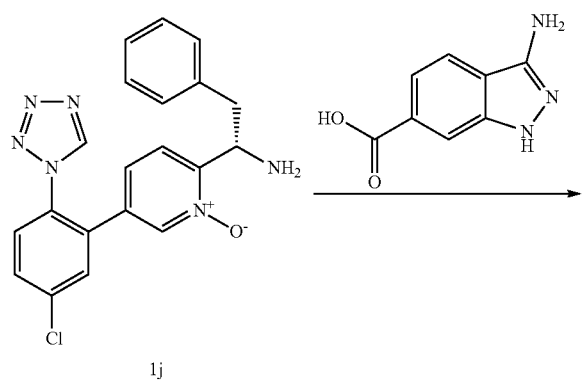

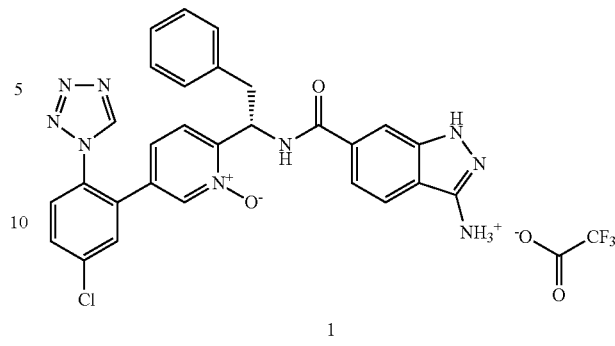

Compound 1j (41.0 mg, 0.105 mmol), 3-amino-1H-indazole-6-carboxylic acid (20.0 mg, 0.116 mmol), and HATU (60.0 mg, 0.158 mmol) were suspended in DMF (2 mL), and DIEA (110 µl, 0.630 mmol) was added. After stirring at ambient temperature overnight the mixture was purified by reverse phase HPLC using Waters Sunfire C18, 5µ, 19×100 mm column with gradient of 20-55% CH$_3$CN (0.16% TFA modifier) to afford the title compound (1). LC-MS [M+H]: m/z 552.3.

Example 2

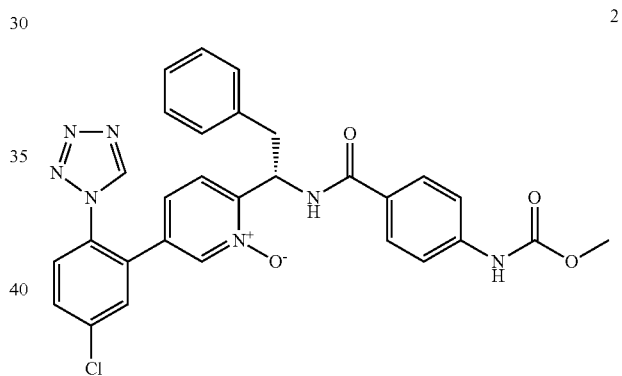

Example 2: (S)-5-(5-chloro-2-(1H-tetrazol-1-yl)phenyl)-2-(1-(4-((methoxycarbonyl)amino)benzamido)-2-phenylethyl)pyridine 1-oxide

Step 1: Preparation of methyl (4-((1-(5-bromopyridin-2-yl)-2-phenylethyl)carbamoyl)phenyl)carbamate (2a)

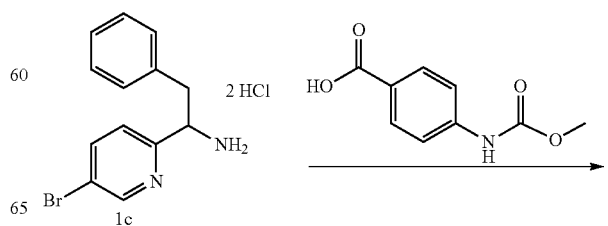

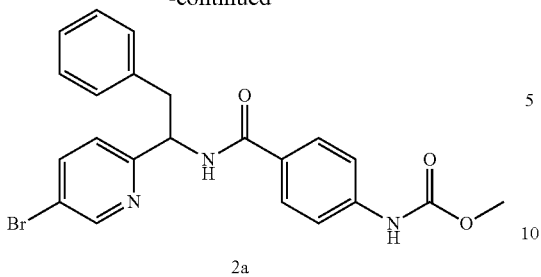

2a

To a solution of 1c (82.0 mg, 0.234 mmol), 4-[(methoxycarbonyl)amino]benzoic acid (54.9 mg, 0.281 mmol), and HATU (134 mg, 0.351 mmol) in DMF (3 mL) was added DIEA (245 μl, 1.41 mmol). After stirring at ambient temperature overnight the mixture was diluted with EtOAc, washed with satd. aq. LiCl solution, H₂O, and brine. The organic layer was dried over MgSO₄, filtered, and concentrated in vacuo, and the residue was purified by silica gel column chromatography using a gradient of 0-60% EtOAc/Hexanes as eluent to provide the title compound (2a) as the major isomer. LC-MS [M+H]: m/z 454.0.

Step 2: Preparation of methyl (4-((1-(5-(2-amino-5-chlorophenyl)pyridin-2-yl)-2-phenylethyl)carbamoyl)phenyl)carbamate (2b)

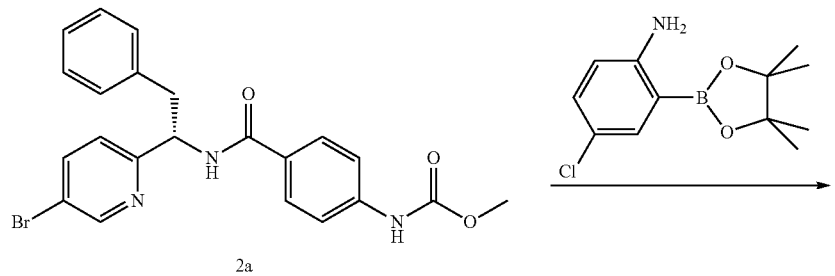

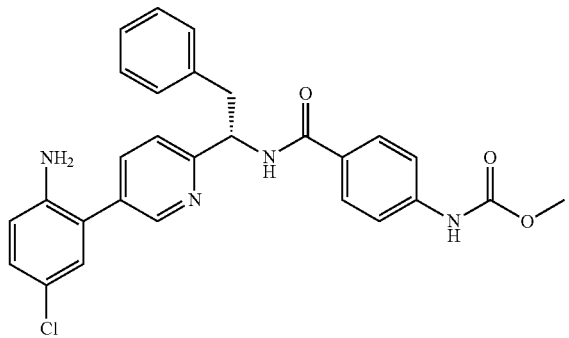

2b

Compound 2a (109 mg, 0.240 mmol), 2-amino-5-chlorophenylboronic acid, pinacol ester (66.9 mg, 0.264 mmol), PdCl₂(dppf) (35.1 mg, 0.048 mmol), and cesium fluoride (109 mg, 0.720 mmol) were suspended in 1,4-dioxane (3.5 mL) in a sealed tube equipped with a septum. A stream of N₂ gas was bubbled through the solution for 5 min and the mixture was heated at 110° C. for 1 h. The mixture was diluted with EtOAc, washed with H₂O, brine, dried over MgSO₄, filtered, and concentrated in vacuo. The residue was purified by silica gel column chromatography using a gradient of 0-100% EtOAc/Hexanes as eluent to provide the title compound (2b) as the major isomer. LC-MS [M+H]: m/z 501.4. ¹H NMR (CHCl₃-d, 500 MHz): δ$_H$ 8.65 (1H, d, J=2.2 Hz), 7.82 (2H, d, J=8.5 Hz), 7.64 (1H, dd, J=8.0, 2.2 Hz), 7.52-7.47 (3H, m), 7.25-7.19 (3H, m), 7.17 (1H, s), 7.10-7.04 (3H, m), 6.74 (2H, t, J=12.4 Hz), 5.57-5.53 (1H, m),), 3.82 (3H, s), 3.68 (2H, s), 3.42 (1H, dd, J=13.3, 5.6 Hz), 3.22 (1H, dd, J=13.3, 8.0 Hz).

Step 3: Preparation of methyl (4-((1-(5-(5-chloro-2-(1H-tetrazol-1-yl)phenyl)pyridin-2-yl)-2-phenyl-ethyl)carbamoyl)phenyl)carbamate (2c)

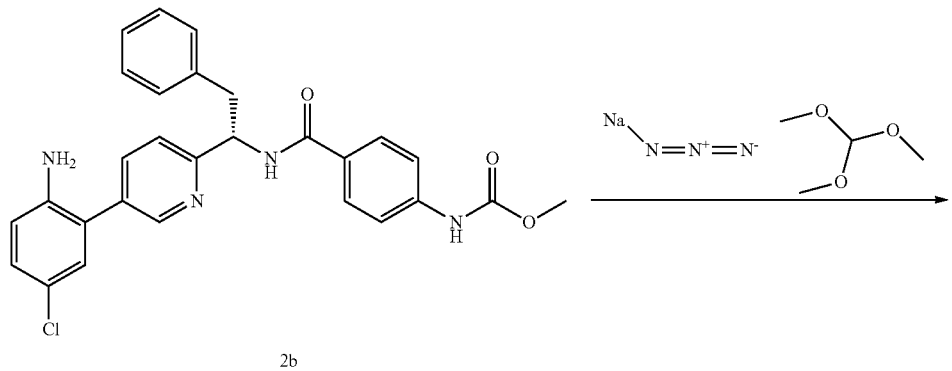

Compound 2b (102 mg, 0.204 mmol), sodium azide (39.7 mg, 0.611 mmol), and trimethoxymethane (67.5 μl, 0.611 mmol) were suspended in acetic acid (2.0 mL). A stream of N₂ was passed over the solution, the vessel was sealed and the mixture was heated at 90° C. for 1.5 h. The mixture was cooled, partitioned between EtOAc and water, and the layers were separated. The organic phase was washed with brine, dried over MgSO₄, filtered, concentrated in vacuo, and the residue was purified by silica gel column chromatography using a gradient of 0-100% EtOAc/Hexanes as eluent to provide the title compound (2c) as the major isomer. LC-MS [M+H]: m/z 554.0. $^1$H NMR (CH$_3$OH-d$_4$, 500 MHz): δ$_H$ 9.23 (1H, s), 8.32 (1H, d, J=2.2 Hz), 7.75-7.69 (5H, m), 7.53 (2H, d, J=8.5 Hz), 7.47 (1H, dd, J=8.1, 2.3 Hz), 7.28-7.11 (6H, m), 5.41 (1H, t, J=7.5 Hz), 3.77 (3H, s), 3.31-3.26 (1H, m), 3.22-3.17 (1H, m).

Step 4: Preparation of (S)-5-(5-chloro-2-(1H-tetrazol-1-yl)phenyl)-2-(1-(4-((methoxycarbonyl)amino)benzamido)-2-phenylethyl)pyridine 1-oxide (2)

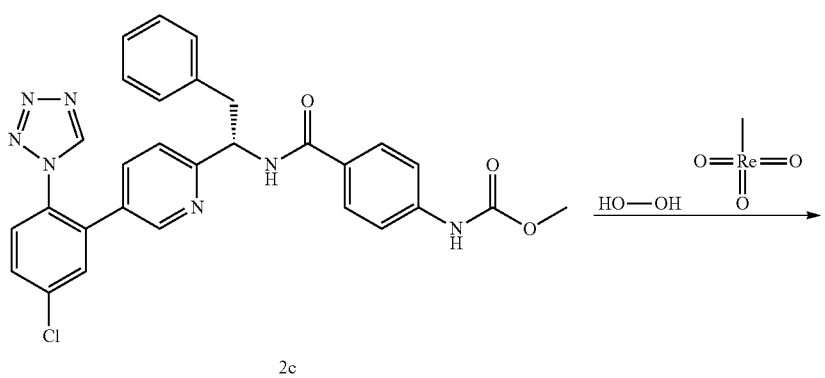

-continued

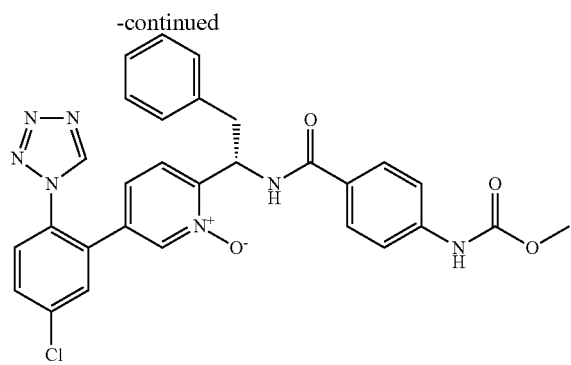

2

To a solution of 2c (86.0 mg, 0.155 mmol) in MeOH (2.0 mL) was added methyltrioxorhenium(VII) (19.4 mg, 0.078 mmol) followed by dropwise addition of 35% aq. hydrogen peroxide (68.0 μl, 0.776 mmol). After stirring at ambient temperature for 30 min an additional amount of 35% aq. hydrogen peroxide (30.0 μL, 0.340 mmol) was added. After 10 min, the reaction was quenched with 10% aq. NaHSO$_3$, and the mixture diluted with EtOAc. The layers were separated and the organic layer was washed with 10% aq. NaHSO$_3$ and brine. The orgainc layer was dried over MgSO$_4$, filtered, concentrated in vacuo, and the residue purified by silica gel column chromatography using a gradient of 0-100% EtOAc/Hexanes as eluent. Further purification by chiral SFC OJ-H column (21×250 mm) using CO$_2$/MeOH as eluent to afford the title compound (2). LC-MS [M+H]: m/z 570.1.

By using the procedures described above, and appropriate starting materials, the following compounds were synthesized.

| Ex | Structure | MS (M + 1) | Human FXI$_a$ Ki (nM) | Human Plasma Kallikrein Ki (nM) |
|---|---|---|---|---|
| 1 | 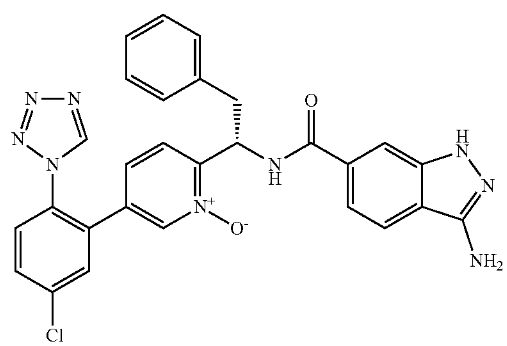 [SMILES: Nc1n[nH]c2cc(C(=O)N[C@@H](Cc3ccccc3)c3ccc(-c4cc(Cl)ccc4-n4cnnn4)c[n+]3[O-])ccc12] | 552.3 | 0.9 | 25 |
| 2 | 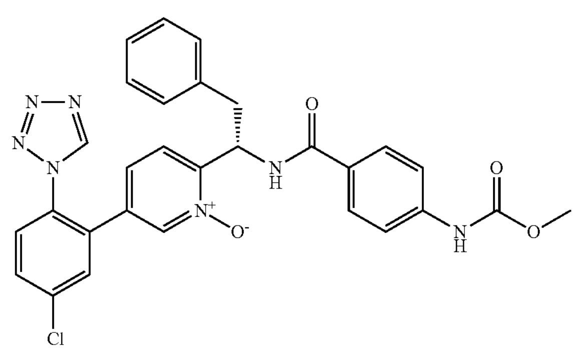 [SMILES: COC(=O)Nc1ccc(C(=O)N[C@@H](Cc2ccccc2)c2ccc(-c3cc(Cl)ccc3-n3cnnn3)c[n+]2[O-])cc1] | 570.4 | 3.6 | 105 |

-continued
| Ex | Structure | MS (M + 1) | Human FXI$_a$ Ki (nM) | Human Plasma Kallikrein Ki (nM) |
|---|---|---|---|---|
| 3 | 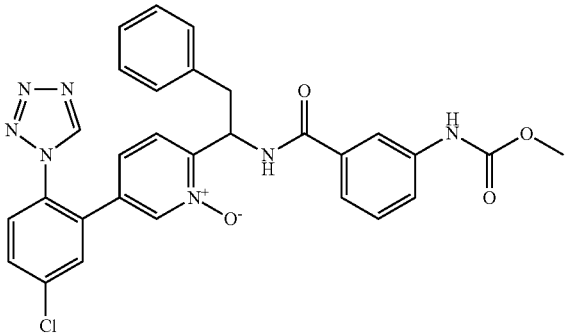 [SMILES: COC(=O)Nc1cccc(C(=O)NC(Cc2ccccc2)c2ccc(-c3cc(Cl)ccc3-n3cnnn3)c[n+]2[O-])c1] | 570.4 | 144 | n.d. |
| 4 | 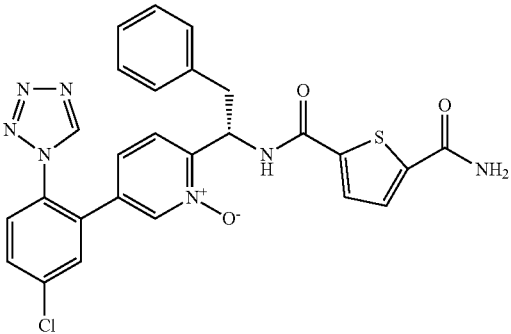 [SMILES: NC(=O)c1ccc(C(=O)N[C@@H](Cc2ccccc2)c2ccc(-c3cc(Cl)ccc3-n3cnnn3)c[n+]2[O-])s1] | n.d. | 1.3 | 36 |
| 5 | 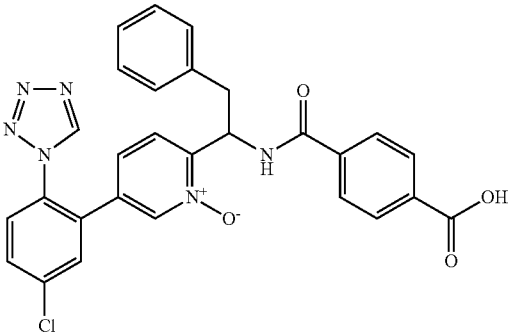 [SMILES: O=C(O)c1ccc(C(=O)NC(Cc2ccccc2)c2ccc(-c3cc(Cl)ccc3-n3cnnn3)c[n+]2[O-])cc1] | 541.2 | 83 | n.d. |
| 6 | 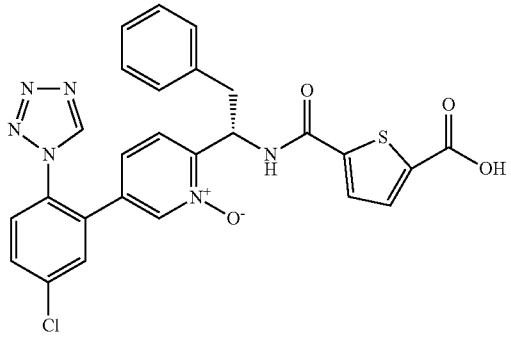 [SMILES: O=C(O)c1ccc(C(=O)N[C@@H](Cc2ccccc2)c2ccc(-c3cc(Cl)ccc3-n3cnnn3)c[n+]2[O-])s1] | 547.2 | 6.9 | 219 |

-continued

| Ex | Structure | MS (M + 1) | Human FXIa Ki (nM) | Human Plasma Kallikrein Ki (nM) |
|---|---|---|---|---|
| 7 | 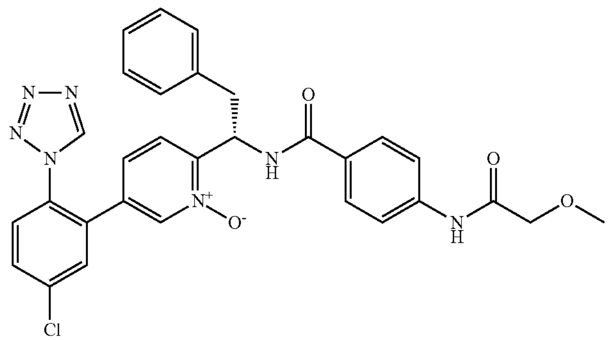 [SMILES: COCC(=O)Nc1ccc(C(=O)N[C@@H](Cc2ccccc2)c2ccc(-c3cc(Cl)ccc3-n3cnnn3)c[n+]2[O-])cc1] | 584.2 | 20 | 516 |

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM $CaCl_2$, and 0.1% PEG 8000 (polyethylene glycol; JT Baker or Fisher Scientific). Determinations were made using purified human Factor XIa at a final concentration of 40 pM (Sekisui Diagnostics) and he synthetic substrate, Z-Gly-Pro-Arg-AFC, TFA salt (Sigma #C0980) at a concentration of 10004.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_0$) or presence of inhibitor ($V_i$) were measured. Assuming competitive inhibition, and that unity is negligible compared $K_m/[S]$, [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_0/V_i$ on [I] shown in the following equation.

$$V_0/V_i=1+[I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Kallikrein determinations were made in 50 mM HEPES buffer at pH 7.4 containing 150 mM NaCl, 5 mM $CaCl_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K-P-R-AFC (Sigma #C6608) at a concentration of 100 mM.

Activity assays were performed by diluting a stock solution of substrate at least tenfold to a final concentration≤0.2 Km into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). $IC_{50}$ was determined by inflection point from a four parameter logistic curve fit. Ki was calculated using the Cheng Prusoff equation, $Ki=IC_{50}/(1+([S]/Km))$.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

What is claimed is:

1. A compound of the formula:

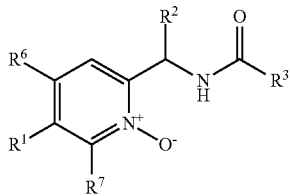

wherein $R_1$ is aryl or heteroaryl, wherein said aryl and heteroaryl groups are optionally substituted with one to three substituents independently selected from the group consisting of halo, nitro, cyano, oxo, $R^4$, $OR^4$, $C(O)R^4$, $C(O)OR^4$, $NR^4R^5$, $C_{1-3}$ alkyl-$NR^4R^5$, NHC(O)$R^4$, NHC(O)O$R^4$, $C_{3-6}$ cycloalkyl and heteroaryl (which is optionally substituted with halo, cyano, C(O)$NR^4R^5$ or $R^4$);

$R^2$ is hydrogen or $CH(R^{2a})(R^{2b})$;

$R^{2a}$ is $C_{1-6}$ alkyl, aryl, heteroaryl, $C_{3-6}$ cycloalkyl or heterocyclyl, wherein said alkyl group is optionally substituted with one to three substituents independently selected from the group consisting of halo, cyano and $OR^4$, and wherein said aryl, heteroaryl, cycloalkyl and heterocyclyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, $C(O)R^4$, $C(O)OR^4$, $C(O)NR^4R^5$, $NR^4R^5$, NHC(O)$R^4$, NHC(O)O$R^4$, NHC(O)$C_{1-4}$alkyl-$OR^4$ and heteroaryl;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is hydrogen, cyano, halo, $R^4$ or $OR^4$;

$R^7$ is hydrogen, cyano, halo, $R^4$ or $OR^4$;

or a pharmaceutically acceptable salt thereof.

2. The compound of claim 1 of the formula:

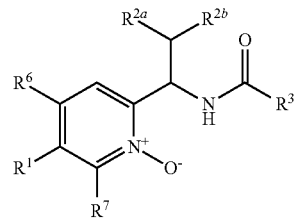

wherein $R^1$ is aryl or heteroaryl, wherein said aryl and heteroaryl groups are optionally substituted with one to three substituents independently selected from the group consisting of halo, nitro, cyano, oxo, $R^4$, $OR^4$, $C(O)R^4$, $C(O)OR^4$, $NR^4R^5$, $C_{1-3}$ alkyl-$NR^4R^5$, NHC(O)$R^4$, NHC(O)O$R^4$, $C_{3-6}$ cycloalkyl and heteroaryl (which is optionally substituted with $R^4$);

$R^{2a}$ is $C_{1-6}$ alkyl, aryl, heteroaryl, $C_{3-6}$ cycloalkyl or heterocyclyl, wherein said alkyl group is optionally substituted with one to three substituents independently selected from the group consisting of halo, cyano and $OR^4$, and wherein said aryl, heteroaryl, cycloalkyl and heterocyclyl groups are optionally substituted with one to three substituents independently selected from the group consisting of halo, nitro, cyano, oxo, $R^4$ and $OR^4$;

$R^{2b}$ is hydrogen or $C_{1-6}$ alkyl, which is optionally substituted with one to three substituents independently selected from the group consisting of halo, hydroxy and cyano;

$R^3$ is aryl, heteroaryl, $C_{3-10}$ cycloalkyl or heterocyclyl, wherein said aryl, heteroaryl, cycloalkyl and heterocyclyl groups are optionally substituted with one to three substituents independently selected from the group consisting of halo, nitro, cyano, oxo, $R^4$, $OR^4$, $C(O)R^4$, $C(O)OR^4$, $C(O)NR^4R^5$, $NR^4R^5$, NHC(O)$R^4$, NHC(O)O$R^4$, NHC(O)$C_{1-4}$alkyl-$OR^4$ and heteroaryl;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^6$ is hydrogen, cyano, halo, $R^4$ or $OR^4$;

$R^7$ is hydrogen, cyano, halo, $R^4$ or $OR^4$;

or a pharmaceutically acceptable salt thereof.

3. The compound of claim 1 wherein $R^1$ is phenyl, which optionally is substituted with one to three substituents independently selected from the group consisting of chloro, fluoro, $C_{3-6}$ cycloalkyl and heteroaryl (which is optionally substituted with $R^4$); or a pharmaceutically acceptable salt thereof.

4. The compound of claim 1 wherein $R^1$ is phenyl, which optionally is substituted with two or three substituents independently selected from the group consisting of chloro and tetrazolyl; or a pharmaceutically acceptable salt thereof.

5. The compound of claim 1 wherein $R^{2a}$ is phenyl, which optionally is substituted with one to three halo, and $R^{2b}$ is hydrogen; or a pharmaceutically acceptable salt thereof.

6. The compound of claim 1 wherein $R^3$ is aryl or heteroaryl, wherein said aryl and heteroaryl groups are optionally substituted with one to three substituents independently selected from the group consisting of $C(O)OR^4$, $C(O)NR^4R^5$, $NR^4R^5$, NHC(O)O$R^4$, NHC(O)$C_{1-4}$alkyl-$OR^4$; or a pharmaceutically acceptable salt thereof.

7. The compound of claim 6 wherein R³ is phenyl, thiophenyl or indazolyl, wherein said phenyl, thiophenyl and indazolyl groups are optionally substituted with C(O)OR⁴, C(O)NR⁴R⁵, NR⁴R⁵, NHC(O)OR⁴, NHC(O)C₁₋₄alkyl-OR⁴; or a pharmaceutically acceptable salt thereof.

8. The compound of claim 1 selected from:

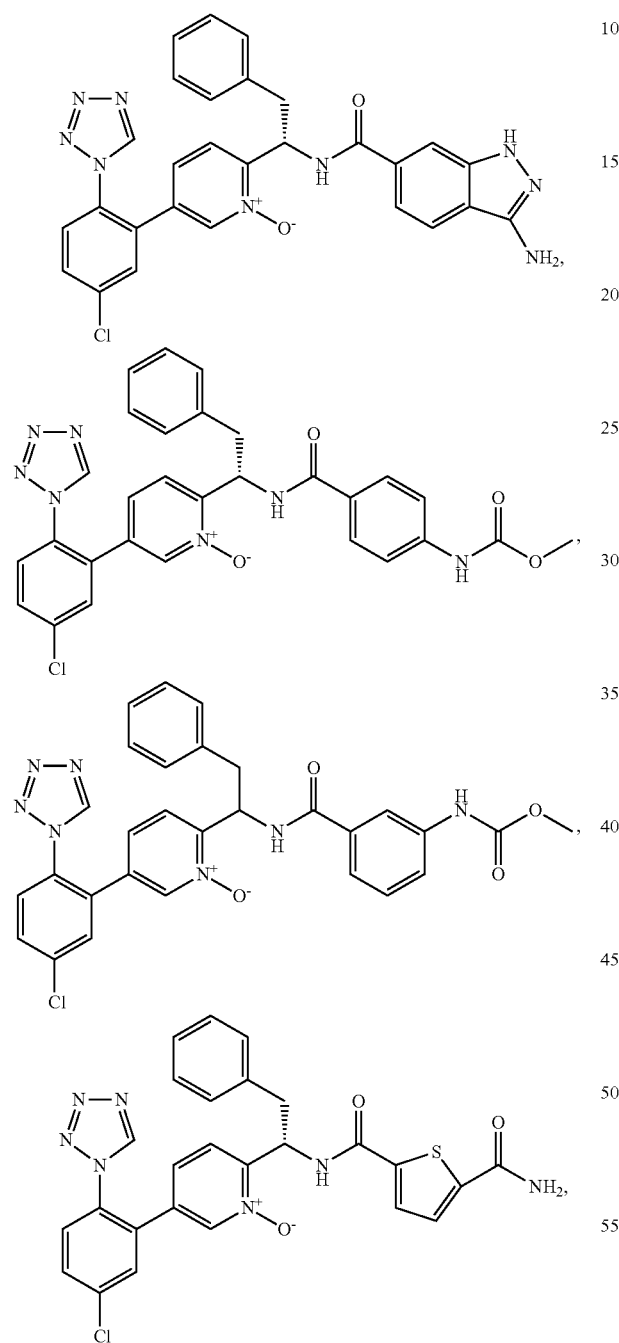

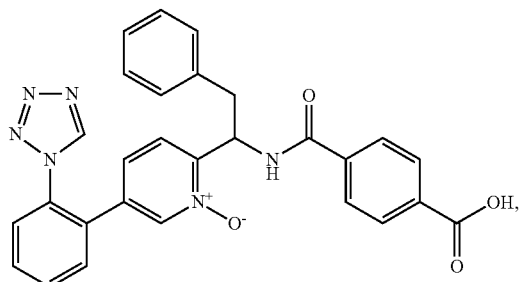

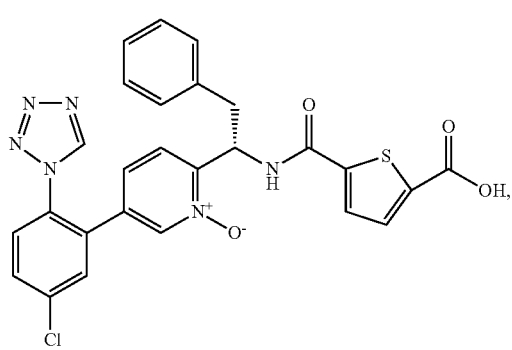

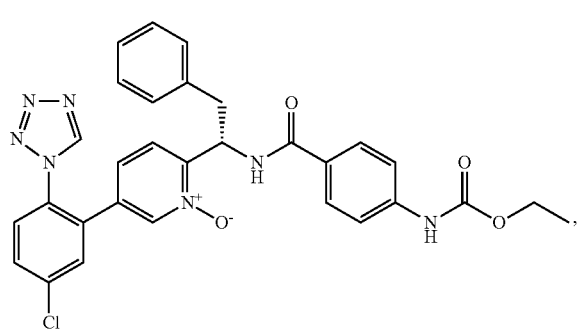

or a pharmaceutically acceptable salt thereof.

9. A pharmaceutical composition comprising a compound of claim 1 or a pharmaceutically acceptable salt thereof and a pharmaceutically acceptable carrier.

10. A method for inhibiting thrombus formation in blood or treating thrombus formation in blood comprising administering a composition of claim 9 to a mammal in need of thereof.

* * * * *